United States Patent [19]

Serban et al.

[11] 4,064,262

[45] Dec. 20, 1977

[54] S-METHYL 3-FURFURYLIDENE-2-METHYL-DITHIOCARBAZATE AND ITS USE AS A FUNGICIDE

[75] Inventors: Alexander Serban, Doncaster; Richard Burridge Warner, Ringwood; Keith Thomas Alcock, Boronia, all of Australia

[73] Assignee: ICI Australia Limited, Melbourne, Australia

[21] Appl. No.: 673,544

[22] Filed: Apr. 5, 1976

[51] Int. Cl.² .................... A01N 9/28; C07D 307/34

[52] U.S. Cl. ............................... 424/285; 260/347.2
[58] Field of Search ................. 260/347.2; 424/285

[56] References Cited

U.S. PATENT DOCUMENTS 3,479,343  11/1969  Johnston .................. 260/347.2 X

*Primary Examiner*—Leonard Schenkman
*Attorney, Agent, or Firm*—Cushman, Darby & Cushman

[57] ABSTRACT

The compound S-methyl 3-furfurylidene-2-methyl-dithiocarbazate and its use as a fungicide.

8 Claims, No Drawings

S-METHYL 3-FURFURYLIDENE-2-METHYL-DITHIOCARBAZATE AND ITS USE AS A FUNGICIDE

This invention relates to a compound having fungicidal activity, and to processes for controlling or eradicating fungi using this compound.

Accordingly we provide the compound S-methyl 3-furfurylidene-2-methyl-dithiocarbazate.

The compound may be made by any of the following methods:

A. 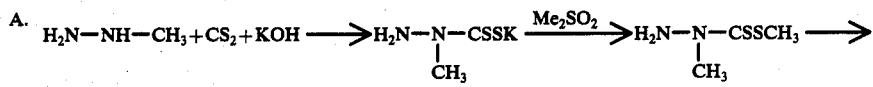
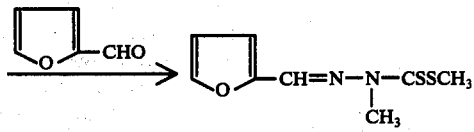

B.
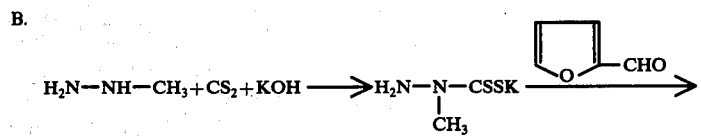
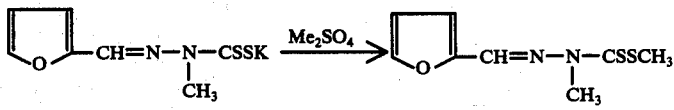

C.
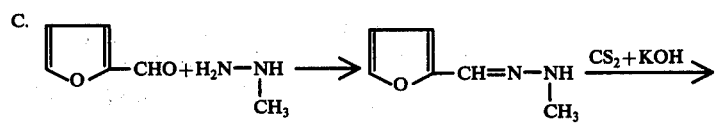
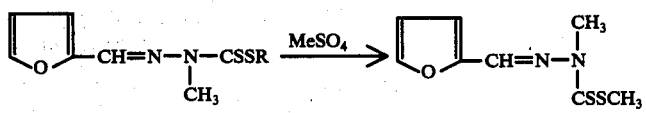

D. 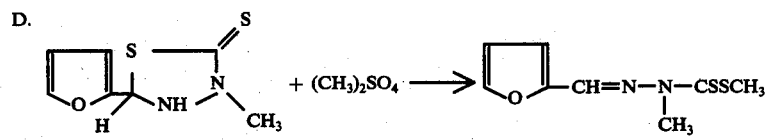

E. 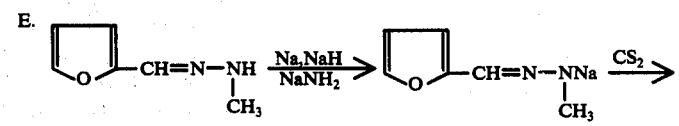
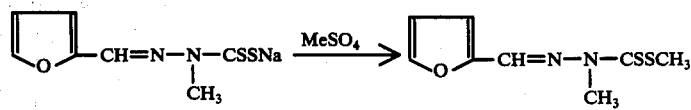

F. 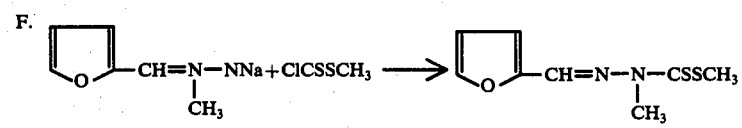

G. 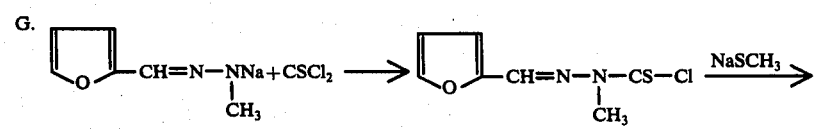
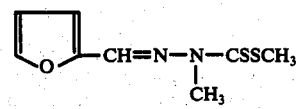

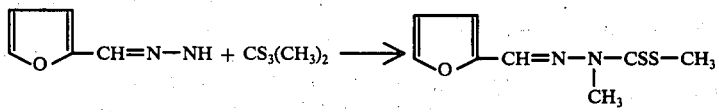

In a further embodiment of our invention we provide a process of eradicating undesired fungi which process comprising treating media infested with fungi with compositions containing S-methyl 3-furfurylidene-2-methyldithiocarbazate.

It is to be understood that the fungicidally active compositions of this invention may comprise, in addition to the active ingredient described hereinabove, one or more other compounds having fungicidal activity.

The compound and compositions of the invention may be used as foliar sprays for the control of fungi on plants but we have found that they are particularly useful as seed dressings.

Accordingly in yet a further embodiment of our invention we provide a process of treating seeds, which process comprises treating seeds prior to sowing with a composition containing fungicidally effective amount of S-methyl 3-furfurylidene-2-methyl-dithiocarbazate.

In particular the present invention relates to a process of treating seeds to control or eradicate the incidence of fungi of the families Tilletia and Ustilago thereon or therein.

The fungi Tilletia and Ustilago are diseases which may cause heavy damage to grain crops such as wheat and barley. It is known in the art that these diseases may be controlled by the application of seed dressing compositions comprising an effective amount of a suitable fungicidal organo-mercury compound. However toxicity and environmental studies have shown that the use of these compounds is highly undesirable, and in addition some species of the fungi Tilletia exhibit resistance to them.

We have now found a compound which is highly effective against bunt and smut and which do not suffer the disadvantages of the prior art active ingredient compounds, and which in addition are highly effective against the resistant species of the fungi Tilletia.

The seed dressings of this invention may comprise, in addition to the S-methyl-3-furfurylidene-2-methyl-dithiocarbazate, one or more other compounds having fungicidal activity especially compounds active against cereal pathogens other than bunt. Such other compounds indicate for example fungicides such as, e.g., Mancozeb, Thiram, 8-hydroxy quinoline an insecticides such as, e.g., Lindane, Malathion.

Especially useful compositions for use as seed dressing compositions comprise from 1 to 90% w/w preferably from 2.5% w/w to 75% w/w of the S-methyl 3-furfurylidene-2-methyl dithiocarbazate.

Our compositions may be formulated in the form of dusting powders or granules wherein the active ingredient is mixed with a solid inert carrier. Suitable solid inert carriers may be, for example, kaolin, powdered chalk, talcs, kieselguhr, dolomite, calcium carbonate, powdered magnesia, Fuller's earth, gypsum, Hewitt's earth, diatomaceous earth, china clay, bentonite, and other colloidal clays.

Alternatively the seed dressing compositions may be in the form of dispersible powder or granules comprising, in addition to the active ingredient an inert carrier comprising a wetting agent to facilitate the dispersion of the powder or granules in liquids. Such powders or granules may include fillers, suspending agents and the like. The preferred dispersible powders comprise the active ingredient mixed with a finely ground colloidal clay together with a dispersing agent.

Suitable dispersing agents are known from the prior art and may be of the cationic, anionic or non-ionic type. Suitable agents of the cationic type include for example quaternary ammonium compounds such as cetyltrimethylammonium bromide. Suitable agents of the anionic type include for example soaps, salts of aliphatic monoesters of sulphuric acid, for example sodium lauryl sulphate, salts of sulphonated aromatic compounds, for example sodium dodecyl-benzene sulphonate, sodium, calcium, or ammonium lignosulphonate, butylnaphthalene sulphonate and a mixture of the sodium salts of di-isopropyl and triisopropylnaphthalene sulphonic acids. Suitable agents of the non-anionic type include for example the condensation products of an alkykene oxide such as ethylene oxide or propylene oxide with fatty alcohols such as oleyl alcohol or cetyl alcohol, or with alkylphenols such as octyl-phenol, nonyl-phenol and octyl-cresol. Other non-ionic agents are the partial esters derived from long chain fatty acids and hexitol anhydrides, the condensation products of the said partial esters with an alkylene oxide such as ethylene oxide or propylene oxide and the lecithins.

Suitable suspending agents are for example, hydrophilic colloids, for example polyvinyl pyrrolidone and sodium carboxymethyl cellulose, and the vegetable gums, for example gum acacia and gum tragacanth.

We have found that deposition of a seed dressing composition containing S-methyl 3-furfurylidene-2-methyldithiocarbazate in an amount of from 50 to 1500 ppm effectively controls or prevent fungal growth to some extent at least.

For economic control of Tilletia sp. we prefer that seeds are treated so that they contain on their surface from 250 to 1500 ppm of the S-methyl 3-furfurylidene-2-methyl dithiocarbazate based on the weight of the seed.

Our invention is illustrated by, but no way limited to, the following examples.

EXAMPLE 1

This example describes the preparation of S-methyl 3-furfurylidene-2-methyl-dithiocarbazate according to the equation i.e.

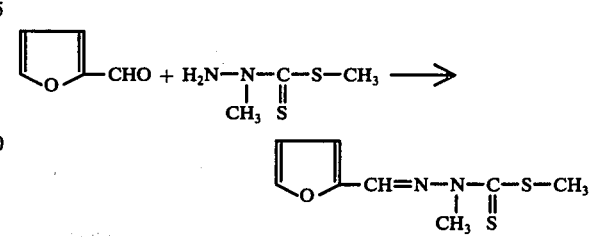

Acetic acid (5 mls) was added to 50 ml of ethanol, this solution was warmed, and 2.7 g of S-methyl-2-methyl-dithiocarbazate was added with stirring. Furfuraldehyde (1.9 g) was added and a crystalline precipitate was obtained which was re-crystallized from ethanol yielding 3.3 g of S-methyl 3-furfurylidene-2-methyl-dithiocarbazate melting at 98° C. The identity of the product was confirmed by mass spectrometry. On further recrystallization from ethanol and charcoal the melting point increased to 104° C.

EXAMPLE 2

This example describes the fungicidal action of compositions according to the present invention in vitro.

To a 1 ml volume of toluene was added 0.004 g of S-methyl 3-furfurylidene-2-methyl-dithiocarbazate and 0.02 g of a 1:1 mixture by weight of "Alkanate" CS ("Alkanate" CS is a Registered Trade Mark of ICI Australia Ltd for a proprietary anionic surface active composition) and "Teric" 200 ("Teric" is a Registered Trade Mark of ICI Australia Ltd for nonionic surface active compositions comprising alkylphenol/alkylene oxide condensates).

This solution was then further diluted with water and mixed with molten agar to give weight per volume concentrations of active ingredient compound of 0.4, 2 and 10 ppm in the final product.

The prepared agar mixtures were poured into petri dishes, allowed to solidify, and were then inoculated with spores of *Tilletia foetida*. A petri dish containing an agar composition comprising no active ingredient was prepared in a similar manner.

In addition petri dishes containing agar compositions comprising as active ingredient "Vitavax" ("Vitavax" is a Registered Trade Mark of Uniroyal Inc for fungicidal compositions comprising as active ingredient, 5, 6-dihydro-2-methyl-1, 4-oxathiin-3-carbox-anilide) were prepared and inoculated substantially in the manner described above. After incubation of the inoculated slides at 10° to 18° C for 7 days of spores was observed. The control obtained is shown in Table I below.

TABLE 1

| Active Ingredient Compound | % Inhibition of Spores (Rating*)-Concentration of Active Ingredient (ppm). | | |
|---|---|---|---|
| | 10 | 2 | 0.4 |
| ⟨furyl⟩—CH=N—N(CH$_3$)—C(=S)—S—CH$_3$ | 3 | 3 | 2 |
| "Vitavax" | 3 | 1 | 0 |
| Control - No Active Ingredient | 0 | 0 | 0 |

*Rating
3 = 90 – 100% Inhibition of spores
2 = 60 – 90% Inhibition of spores
1 = 30 – 60% Inhibition of spores
0 = 0 – 30% Inhibition of spores

EXAMPLE 3

This example describes the fungicidal action of a composition according to the present invention against the fungi *Tilletia foetida* (B.H.C. susceptible) and *Tilletia foetida* (B.H.C. resistant) under field conditions.

Samples of wheat seed (c.v. Olympic) were inoculated with spores of each of the fungal species *Tilletia foetida* (B.H.C. susceptible) and *Tilletia foetida* (B.H.C. resistant) in the following manner. Spores of each fungus were admixed with wheat seed at a rate of 0.4 g. of spores per 99.6 g. of seed and the mixtures were blended by rotation in sealed containers on the rollers of a ball mill for twenty minutes.

The samples of inoculated seed were then dressed with a fungicidal composition according to the present invention and comprising 50% w/w of S-methyl 3-furfurylidene-2-methyldithiocarbazate, 3% w/w of ethylene glycol, 5% w/w of "Celite" 298, and 42% w/w of china clay, by application of the said fungicidal composition at a rate of 1 g per kg of inoculated seed and blending by rotation in a sealed container on the rollers of a ball mill for twenty minutes to produce uniform products containing 500 ppm by weight of active ingredient compound.

Each sample of dressed seed was then sown through a seed drill in 4 single row plots each 22 yards in length. The seed was then allowed to germinate and the wheat plants were allowed to mature. At harvest the seed heads were collected and the control of disease assessed. The percentage of diseased heads is presented in Table II below.

For purposes of comparison the sowing procedure described above was substantially repeated except that the dressed seed was replaced by samples of seed inoculated with each of the fungi described above but not treated with a fungicidal composition.

The percentage of diseased heads obtained in these comparative tests is also presented in Table II below.

TABLE 11

| Active ingredient | Concentration (ppm) | Control of fungi - % of diseased heads | |
|---|---|---|---|
| | | *Tilletia Fortida* (H.C.B. Susceptible) | *Tilletia foetida* (H.C.B. Resistant) |
| ⟨furyl⟩—CH=N—N(CH$_3$)—C(=S)—S—CH$_3$ | 500 | 0.35 | 0 |
| Control - No active ingredient | — | 36.88 | 10.47 |

EXAMPLE 4

This example describes the fungicidal activity of compositions of the present invention against *Puccinia coronata* (oat rust).

Two hundred milliliters of an aqueous composition comprising 0.05% w/v of S-methyl 3-furfurylidene-2-methyl dithiocarbazate was sprayed onto a pot of 30 5 inches tall oat plants. Twenty four hours after spraying the plants were inoculated with *Puccinia coronata* (oat rust) by dusting them with a concentrated spore suspension taken from infected plant material. After inoculation the oats were placed in a high humidity cabinet for 24 hours and then returned to the glass house. The plants were assessed eight days after inoculation and found to be substantially free of disease.

EXAMPLES 5 AND 6

This example describes the control of the fungi *Rhizoctonia solani* (early blight of tomatoes), *Ceratocystis poradoxa* (pineapple disease of sugar cane) and *Venturia inequalis* (black spot or apple scab).

Small quantities of an aqueous ball milled suspension of S-methyl 3-furfurylidene-2-methyl-dithiocarbazate were mixed with 20 milliliter volumes of an aqueous composition comprising 0.5% w/w of potato dextrose agar and 0.5% w/w of water agar and the mixtures were then poured into petri dishes and allowed to set. Sufficient of the aqueous suspension was included to provide agar compositions having active ingredient concentrations of 10 ppm by weight and 25 ppm by weight in the final agar compositions.

A one centimeter cube of agar infected with *Rhizoctonia solani, Ceratocystis poradoxa* or *Venturia inequalis* was then placed in each petri dish and the growth of the fungi was assessed four days later. The results are presented in Table III below.

TABLE III

| Fungal Species | % Inhibition of Spores (rating)* Concentration of Active Ingredient (ppm) | |
|---|---|---|
| | 25 | 10 |
| *Rhizoctonia solani* | 3 | 3 |
| *Ceratocystis poradoxa* | 3 | 3 |
| *Venturia inequalis* | — | 3 |

*As for Example 2

EXAMPLE 7

Analogues of S-methyl 3-furfurylidene-2-methyl-dithiocarbazate as shown in Table IV below were prepared by reaction of a carbonyl compound (A) with various dithiocarbazates (B) according to the method of Example 1.

TABLE IV

| Structure | A | B | m.p. |
|---|---|---|---|
| furyl–C(Me)=N–N(Me)–C(=S)–S–Me | furyl–C(Me)=O | H₂N–N(Me)–C(=S)–S–Me | 89° |
| furyl–CH=N–N(Me)–C(=S)–S–Et | furyl–CHO | H₂N–N(Me)–C(=S)–S–Et | 93° |
| furyl–CH=N–NH–C(=S)–S–Me | furyl–CHO | H₂N–NH–C(=S)–S–Me | 150° |
| furyl–CH=N–NH–C(=S)–S–Et | furyl–CHO | H₂N–NH–C(=S)–S–Et | 131° |

EXAMPLE 8

This example describes the fungicidal action of the analogues prepared in Example 7 in the field under natural conditions.

Wheat seed (c.v. Olympic), was inoculated with a mixture of equal amounts of *Tilletia foetida* spores HCB resistant and HCB susceptible and *Tilletia caries* by admixing 1 g of the mixed spores with each lb of seed and then tumble mixing the mixture for 20 minutes. Separate samples of inoculated seed was then dressed with a composition by comprising 50% w/w of china clay and 50% w/w of each of the compounds listed in Table V at rates of 0.01 g per 20 g of 0.01 g per 13.3 g of inoculated seed and 0.01 g per 10 g of inoculated seed, and tumble mixing the mixtures until uniform products containing 250 ppm, 375 ppm and 500 ppm compound respectively were obtained.

For each fungicidal composition and at each application rate, dressed seed was then sown through a seed drill in 6 single row plots each 10 feet in length. The seed was then allowed to germinate and the wheat plants allowed to mature. The trials of each treatment rate were carried out in a different part of Victoria.

For purposes of comparison the sowing procedure described above was substantially repeated except that the dressed seed was replaced by untreated inoculated seed.

At harvest the seed heads were collected and the control of the disease assessed. The percentage of diseased heads is shown in Table V below.

TABLE V

| Compound | % disease 500 ppm | 375 ppm | 250 ppm |
|---|---|---|---|
| furyl-CH=N-N(Me)-C(=S)-S-Me | 0.18 | 0.70 | 2.27 |
| furyl-C(Me)-N(Me)-N-C(=S)-S-Me | 25.79 | 40.73 | 25.79 |
| furyl-CH-N(Me)-N-C(=S)-S-Et | 4.67 | 6.28 | 10.06 |
| furyl-CH=N-NH-C(=S)-S-Me | 15.77 | 10.70 | 11.21 |
| furyl-CH=N-NH-C(=S)-S-Et | 15.30 | 17.10 | 14.93 |
| Control (no treatment) | 32.06 | 60.03 | 24.20 |

The results obtained demonstrate that the compounds of Example 7 have activity against *Tilletia foetida* and *Tilletia caries*. However this activity is much less than the activity of the compound of the present invention.

EXAMPLE 9

11.8 g of potassium hydroxide were dissolved in 80 ml of ethanol. After the reaction mixture was cooled to 10°, 9.2 g of methylhydrazine was added and the mixture stirred for 5 minutes.

14.5 g of carbon disulphide were added dropwise keeping the temperature between 10° 14 15°. The reaction mixture was stirred at room temperature for 2 hours. 120 ml of water was added, then 27.8 g of dimethyl sulphate was added dropwise keeping the temperature below 20°. After stirring for 2 hours at room temperature, 18 g of furfuraldehyde was added dropwise and with vigorous stirring, then the reaction mixture was stirred for ½ hour at room temperature. 200 ml of water was added, then the mixture was cooled below 10°, then the precipitate was filtered off, washed with water, and dried at 60° in vacuum. Yield of S-methyl-3-furfurylidene-2-methyl-dithiocarbazate = 36.5 g mp = 100° (90%).

EXAMPLE 10

5.9 g of potassium hydroxide were dissolved in 40 ml of ethanol and the solution cooled to room temperature, then 4.6 g of methylhydrazine was added. After cooling to 10°, 7.25 g of carbon disulphide was added dropwise with stirring, keeping the temperature below 15°. After stirring for 2 hours at room temperature, 9 g of furfural was added dropwise with stirring. Potassium 3-(2-furfurylidene)-2-methyl-dithiocarbazate was formed during stirring for 2 hours at room temperature. 100 ml of ether was added, the suspension was cooled below 10° and the product was filtered off, washed with chilled ether and dried. 12 g of this product was suspended in 150 ml of methanol and 19 g of dimethyl sulphate was added and the mixture was sitrred for 5 hours at room temperature. Water was then added to 500 ml and after stirring for 15 minutes and cooling below 10°, the product was filtered off and washed with water. The product had a m.p. of 103° and was identified as being S-methyl-3-furfurylidene-2-methyl-dithiocarbazate.

EXAMPLE 11

9.8 g methyl hydrazine was stirred with 70 mls absolute ethanol. 19.2 g furfural was added dropwise to the reaction mixture, and stirred at room temperature for 1½ hours.

10.8 g potassium hydroxide (dissolved in 40 mls ethanol) was added all at once, and then 15.2 g carbon disulphide added dropwise (15° C).

The reaction mixture was stirred at room temperature for 16 hours, cooled to 10° C for 1½ hours and filtered. A product with mp 237° was obtained and this was identified by spectroscopic means to be potassium 3-(2-furfurylidene)-2-methyl-dithiocarbazate.

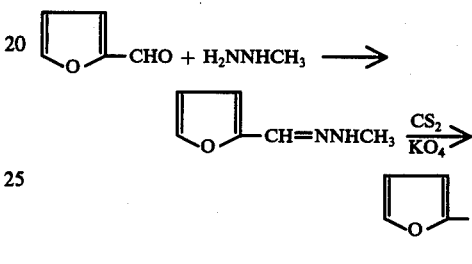

4.8 g of this salt was dissolved in 50 ml of 50% aqueous ethanol then 2.52 g of dimethyl sulphate was added dropwise over 1 hour, and further stirred for 2 hours. After cooling below 10° the product was filtered off, washed in the chilled ethanol and dried. It was identified by spectroscopic means to be S-methyl 3-furfurylidene-2-methyl-dithiocarbazate.

EXAMPLE 12

1 g of 2-(2-furyl)-4-methyl-1,3,4-thidiazolidine-5-thione was dissolved in 50 ml of warm ethanol, and after cooling to room temperature 1.26 g of dimethyl sulphate was added. After stirring for 2.5 hours at 50°, 0.69 g potassium was added, the mixture was heated for 1.5 hours at 50°, then allowed to stand overnight. The reaction mixture was filtered and the filtrate was evaporated to dryness. The residue was recrystallised from ethanol and pure S-methyl 3-furfurylidene- 2-methyl-dithiocarbazate (mp = 103°) was obtained.

We claim:
1. S-methyl 3-furfurylidene-2-methyl-dithiocarbazate.
2. A seed dressing comprising as active ingredient from 1 to 90% w/w of S-methyl 3-furfurylidene-2-methyl-dithiocarbazate and a carrier therefor.
3. A method of treating seeds comprising applying to the seeds prior to sowing a fungicidally effective amount of a seed dressing comprising S-methyl 3-furfurylidene-2-methyl-dithiocarbazate.
4. A seed dressing according to claim 2 containing from 2.5% w/w to 75% w/w of S-methyl 3-furfurylidene-2-methyl-dithiocarbazate.
5. A method of treating seeds according to claim 3 wherein the seed is a cereal infected with Tilletia sp. and wherein the weight of S-methyl 3-furfurylidene-2-methyl-dithiocarbazate deposited on the surface of the seed is in the range from 50 to 1500 ppm of the weight of the seed.

6. A method of treating seed according to claim 5 wherein the weight of S-methyl 3-furfurylidene-2-methyl-dithiocarbazate deposited on the surface of the seed is in the range of from 230 ppm to 1500 ppm of the weight of the seed.

7. A process of controlling foliar fungi on plants by spraying the foliage of said plants with a composition containing an effective amount of S-methyl 3-furfurylidene-2-methyl-dithiocarbazate.

8. A process according to claim 7 wherein the plants are infected with one of the following fungus diseases: *Puccinia coronata, Rhizoctonia solani, Ceratocystis poradoxa* or *Venturia inequalis.*

* * * * *